(12) United States Patent
Stotz et al.

(10) Patent No.: US 12,102,835 B2
(45) Date of Patent: *Oct. 1, 2024

(54) TRANSMISSION UNIT COMPRISING A TRANSMISSION COIL AND A TEMPERATURE SENSOR

(71) Applicant: KARDION GMBH, Stuttgart (DE)

(72) Inventors: Ingo Stotz, Ditzingen (DE); Samuel Vasconcelos Araujo, Esslingen (DE); Michael Jiptner, Besigheim (DE)

(73) Assignee: Kardion GmbH, Stuttgart (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/231,517

(22) Filed: Aug. 8, 2023

(65) Prior Publication Data

US 2023/0381526 A1   Nov. 30, 2023

Related U.S. Application Data

(63) Continuation of application No. 17/051,400, filed as application No. PCT/EP2019/061321 on May 2, 2019, now Pat. No. 11,752,354.

(30) Foreign Application Priority Data

May 2, 2018  (DE) .......................... 102018206754.6

(51) Int. Cl.
*A61N 1/378* (2006.01)
*A61M 60/165* (2021.01)
(Continued)

(52) U.S. Cl.
CPC ......... *A61N 1/3787* (2013.01); *A61M 60/165* (2021.01); *A61M 60/178* (2021.01);
(Continued)

(58) Field of Classification Search
CPC .... A61N 1/3787; H02J 50/10; A61M 60/165; A61M 60/873; A61M 2205/8243; A61M 2230/005; A61M 2230/50
(Continued)

(56) References Cited

U.S. PATENT DOCUMENTS

| 2,254,698 A | 9/1941 | Hansen, Jr. |
| 3,085,407 A | 4/1963 | Tomlinson |

(Continued)

FOREIGN PATENT DOCUMENTS

| CA | 3 000 581 | 4/2017 |
| CN | 103143072 | 6/2013 |

(Continued)

OTHER PUBLICATIONS

International Search Report and Written Opinion received in PCT Application No. PCT/EP2019/061321, dated Oct. 22, 2019 in 19 pages.

(Continued)

*Primary Examiner* — Alfonso Perez Borroto
(74) *Attorney, Agent, or Firm* — Knobbe, Martens, Olson & Bear, LLP (57) ABSTRACT

The invention relates to a transmitter unit (12) comprising a housing (20), a transmitter coil (18) arranged in the housing (20) for inductively transferring electrical energy to a receiver unit (14) which is provided with a receiver coil (16) and is arranged in the tissue (2) of the body (1) of a patient when the housing (20) having a contact surface (22) is placed on the body (1), and comprising a control device (30) for controlling the operation of the transmitter coil (18). According to the invention, a temperature sensor (26) is provided in the transmitter unit for determining a heating of the tissue (2) of the body (1) caused by the inductive transfer of electrical energy to the receiver unit (14). The invention (Continued)

also relates to methods for determining the temperature ($T_{Korr}$) of the tissue (2) of a body (1) on a surface (38), by which electrical energy is inductively transmitted for supplying an electrical consumer arranged in the tissue (2) of the body (1), and to a method for inductively transferring electrical energy.

20 Claims, 2 Drawing Sheets

(51) Int. Cl.
  *A61M 60/178* (2021.01)
  *A61M 60/205* (2021.01)
  *A61M 60/873* (2021.01)
  *H02J 50/10* (2016.01)

(52) U.S. Cl.
  CPC ........ *A61M 60/205* (2021.01); *A61M 60/873* (2021.01); *H02J 50/10* (2016.02); *A61M 2205/8243* (2013.01); *A61M 2230/005* (2013.01); *A61M 2230/50* (2013.01)

(58) Field of Classification Search
  USPC ........................................................ 307/651
  See application file for complete search history.

(56) References Cited

U.S. PATENT DOCUMENTS

| | | |
|---|---|---|
| 3,614,181 A | 10/1971 | Meeks |
| 3,645,268 A | 2/1972 | Capote |
| 3,747,998 A | 7/1973 | Klein et al. |
| 3,790,878 A | 2/1974 | Brokaw |
| 3,807,813 A | 4/1974 | Milligan |
| 4,441,210 A | 4/1984 | Hochmair et al. |
| 4,888,009 A | 12/1989 | Lederman et al. |
| 4,888,011 A | 12/1989 | Kung et al. |
| 4,896,754 A | 1/1990 | Carlson et al. |
| 5,000,177 A | 3/1991 | Hoffmann et al. |
| 5,195,877 A | 3/1993 | Kletschka |
| 5,289,821 A | 3/1994 | Swartz |
| 5,443,503 A | 8/1995 | Yamane |
| 5,599,173 A | 2/1997 | Chen et al. |
| 5,613,935 A | 3/1997 | Jarvik |
| 5,629,661 A | 5/1997 | Ooi et al. |
| 5,690,674 A | 11/1997 | Diaz |
| 5,713,954 A | 2/1998 | Rosenberg et al. |
| 5,766,207 A | 6/1998 | Potter et al. |
| 5,814,900 A | 9/1998 | Esser |
| 5,843,141 A | 12/1998 | Bischoff et al. |
| 5,888,242 A | 3/1999 | Antaki et al. |
| 6,053,873 A | 4/2000 | Govari et al. |
| 6,058,958 A | 5/2000 | Benkowski et al. |
| 6,149,405 A | 11/2000 | Abe et al. |
| 6,212,430 B1 | 4/2001 | Kung et al. |
| 6,224,540 B1 | 5/2001 | Lederman et al. |
| 6,254,359 B1 | 7/2001 | Aber |
| 6,264,601 B1 | 7/2001 | Jassawalla et al. |
| 6,324,430 B1 | 11/2001 | Zarinetchi et al. |
| 6,324,431 B1 | 11/2001 | Zarinetchi et al. |
| 6,361,292 B1 | 3/2002 | Chang et al. |
| 6,366,817 B1 | 4/2002 | Kung |
| 6,389,318 B1 | 5/2002 | Zarinetchi et al. |
| 6,398,734 B1 | 6/2002 | Cimochowski et al. |
| 6,400,991 B1 | 6/2002 | Kung |
| 6,442,434 B1 | 8/2002 | Zarinetchi et al. |
| 6,445,956 B1 | 9/2002 | Laird et al. |
| 6,471,713 B1 | 10/2002 | Vargas et al. |
| 6,496,733 B2 | 12/2002 | Zarinetchi et al. |
| 6,508,756 B1 | 1/2003 | Kung et al. |
| 6,516,227 B1 | 2/2003 | Meadows et al. |
| 6,527,698 B1 | 3/2003 | Kung et al. |
| 6,530,876 B1 | 3/2003 | Spence |
| 6,540,658 B1 | 4/2003 | Fasciano et al. |
| 6,553,263 B1 | 4/2003 | Meadows et al. |
| 6,561,975 B1 | 5/2003 | Pool et al. |
| 6,592,620 B1 | 7/2003 | Lancisi et al. |
| 6,979,338 B1 | 12/2005 | Loshakove et al. |
| 7,062,331 B2 | 6/2006 | Zarinetchi et al. |
| 7,070,398 B2 | 7/2006 | Olsen et al. |
| 7,155,291 B2 | 12/2006 | Zarinetchi et al. |
| 7,160,243 B2 | 1/2007 | Medvedev |
| 7,338,521 B2 | 3/2008 | Antaki et al. |
| 7,513,864 B2 | 4/2009 | Kantrowitz et al. |
| 7,520,850 B2 | 4/2009 | Brockway |
| 7,762,941 B2 | 7/2010 | Jarvik |
| 7,794,384 B2 | 9/2010 | Sugiura et al. |
| 7,819,916 B2 | 10/2010 | Yaegashi |
| 7,942,805 B2 | 5/2011 | Shambaugh, Jr. |
| 7,959,551 B2 | 6/2011 | Jarvik |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,231,519 B2 | 7/2012 | Reichenbach et al. |
| 8,489,200 B2 | 7/2013 | Zarinetchi et al. |
| 8,608,635 B2 | 12/2013 | Yomtov et al. |
| 8,612,002 B2 | 12/2013 | Faltys et al. |
| 8,620,447 B2 | 12/2013 | D'Ambrosio et al. |
| 8,766,788 B2 | 7/2014 | D'Ambrosio |
| 8,827,890 B2 | 9/2014 | Lee et al. |
| 8,862,232 B2 | 10/2014 | Zarinetchi et al. |
| 8,870,739 B2 | 10/2014 | LaRose et al. |
| 8,900,114 B2 | 12/2014 | Tansley et al. |
| 8,961,389 B2 | 2/2015 | Zilbershlag |
| 9,002,468 B2 | 4/2015 | Shea et al. |
| 9,002,469 B2 * | 4/2015 | D'Ambrosio ......... H02J 7/0068 607/61 |
| 9,071,182 B2 | 6/2015 | Yoshida et al. |
| 9,220,826 B2 | 12/2015 | D'Ambrosio |
| 9,283,314 B2 | 3/2016 | Prasad et al. |
| 9,381,286 B2 | 7/2016 | Spence et al. |
| 9,440,013 B2 | 9/2016 | Dowling et al. |
| 9,456,898 B2 | 10/2016 | Barnes et al. |
| 9,486,566 B2 | 11/2016 | Siess |
| 9,492,600 B2 | 11/2016 | Strueber et al. |
| 9,539,094 B2 | 1/2017 | Dale et al. |
| 9,561,362 B2 | 2/2017 | Malinowski |
| 9,569,985 B2 | 2/2017 | Alkhatib et al. |
| 9,592,397 B2 | 3/2017 | Hansen et al. |
| 9,603,984 B2 | 3/2017 | Romero et al. |
| 9,616,107 B2 | 4/2017 | VanAntwerp et al. |
| 9,713,701 B2 | 7/2017 | Sarkar et al. |
| 9,717,831 B2 | 8/2017 | Schuermann |
| 9,724,083 B2 | 8/2017 | Quadri et al. |
| 9,800,172 B1 | 10/2017 | Leabman |
| 9,833,314 B2 | 12/2017 | Corbett |
| 9,833,611 B2 | 12/2017 | Govea et al. |
| 9,848,899 B2 | 12/2017 | Sliwa et al. |
| 9,974,894 B2 | 5/2018 | Morello |
| 10,143,571 B2 | 12/2018 | Spence et al. |
| 10,463,508 B2 | 11/2019 | Spence et al. |
| 10,732,583 B2 | 8/2020 | Rudser |
| 10,944,293 B2 | 3/2021 | Nakao |
| 11,000,282 B2 | 5/2021 | Schuelke et al. |
| 11,056,878 B2 | 7/2021 | Gao et al. |
| 11,065,437 B2 | 7/2021 | Aber et al. |
| 11,103,715 B2 | 8/2021 | Fort |
| 11,110,265 B2 | 9/2021 | Johnson |
| 11,179,559 B2 | 11/2021 | Hansen |
| 11,224,737 B2 | 1/2022 | Petersen et al. |
| 11,291,826 B2 | 4/2022 | Tuval et al. |
| 11,316,371 B1 | 4/2022 | Partovi et al. |
| 11,317,988 B2 | 5/2022 | Hansen et al. |
| 11,344,717 B2 | 5/2022 | Kallenbach et al. |
| 11,351,359 B2 | 6/2022 | Clifton et al. |
| 11,351,360 B2 | 6/2022 | Rudser et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,389,641 B2 | 7/2022 | Nguyen et al. |
| 11,406,483 B2 | 8/2022 | Wirbisky et al. |
| 11,406,520 B2 | 8/2022 | Lam |

(56) References Cited

U.S. PATENT DOCUMENTS

| | | |
|---|---|---|
| 11,406,802 B2 | 8/2022 | DeGraaf et al. |
| 11,413,443 B2 | 8/2022 | Hodges et al. |
| 11,413,444 B2 | 8/2022 | Nix et al. |
| 11,439,806 B2 | 9/2022 | Kimball et al. |
| 11,471,692 B2 | 10/2022 | Aghassian et al. |
| 11,497,906 B2 | 11/2022 | Grace et al. |
| 11,517,737 B2 | 12/2022 | Struthers et al. |
| 11,517,738 B2 | 12/2022 | Wisniewski |
| 11,517,740 B2 | 12/2022 | Agarwa et al. |
| 11,529,508 B2 | 12/2022 | Jablonsk et al. |
| 11,583,671 B2 | 2/2023 | Nguyen et al. |
| 11,596,727 B2 | 3/2023 | Siess et al. |
| 11,602,624 B2 | 3/2023 | Siess et al. |
| 11,682,924 B2 | 6/2023 | Hansen et al. |
| 11,689,057 B2 | 6/2023 | Hansen |
| 11,699,551 B2 | 7/2023 | Diekhans et al. |
| 11,745,005 B2 | 9/2023 | Delgado, III |
| 11,752,354 B2 | 9/2023 | Stotz et al. |
| 11,804,767 B2 | 10/2023 | Vogt et al. |
| 11,881,721 B2 | 1/2024 | Araujo et al. |
| 2001/0016686 A1 | 8/2001 | Okada et al. |
| 2002/0177324 A1 | 11/2002 | Metzler |
| 2003/0040765 A1 | 2/2003 | Breznock |
| 2003/0125766 A1 | 7/2003 | Ding |
| 2003/0130581 A1 | 7/2003 | Salo et al. |
| 2004/0167410 A1 | 8/2004 | Hettrick |
| 2005/0006083 A1 | 1/2005 | Chen et al. |
| 2005/0107658 A1 | 5/2005 | Brockway |
| 2005/0107847 A1 | 5/2005 | Gruber et al. |
| 2006/0004423 A1 | 1/2006 | Boveja et al. |
| 2006/0190036 A1 | 8/2006 | Wendel et al. |
| 2006/0196277 A1 | 9/2006 | Allen et al. |
| 2007/0129767 A1 | 6/2007 | Wahlstrand |
| 2007/0282209 A1 | 12/2007 | Lui et al. |
| 2008/0015481 A1 | 1/2008 | Bergin et al. |
| 2008/0079392 A1 | 4/2008 | Baarman et al. |
| 2008/0082005 A1 | 4/2008 | Stern et al. |
| 2008/0211455 A1 | 9/2008 | Park et al. |
| 2008/0266922 A1 | 10/2008 | Mumtaz et al. |
| 2009/0010462 A1 | 1/2009 | Ekchian et al. |
| 2009/0024042 A1 | 1/2009 | Nunez et al. |
| 2009/0134711 A1 | 5/2009 | Issa et al. |
| 2009/0198307 A1 | 8/2009 | Mi et al. |
| 2009/0198312 A1 | 8/2009 | Barker |
| 2009/0276016 A1 | 11/2009 | Phillips et al. |
| 2009/0312650 A1 | 12/2009 | Maile et al. |
| 2010/0010582 A1* | 1/2010 | Carbunaru .......... H01M 10/443 607/61 |
| 2010/0191035 A1 | 7/2010 | Kang et al. |
| 2010/0219967 A1 | 9/2010 | Kaufmann |
| 2010/0280568 A1 | 11/2010 | Bulkes et al. |
| 2010/0312310 A1 | 12/2010 | Meskens |
| 2010/0331918 A1* | 12/2010 | DiGiore .......... A61N 1/3787 607/61 |
| 2010/0331920 A1* | 12/2010 | DiGiore .......... A61N 1/3787 607/61 |
| 2011/0071336 A1 | 3/2011 | Yomtov |
| 2011/0137394 A1 | 6/2011 | Lunsford et al. |
| 2011/0224720 A1 | 9/2011 | Kassab et al. |
| 2012/0019201 A1* | 1/2012 | Peterson .......... A61N 1/3787 320/108 |
| 2012/0022645 A1 | 1/2012 | Burke |
| 2012/0050931 A1 | 3/2012 | Terry et al. |
| 2012/0112543 A1 | 5/2012 | van Wageningen et al. |
| 2012/0158074 A1 | 6/2012 | Hall |
| 2012/0212178 A1 | 8/2012 | Kim |
| 2012/0235633 A1 | 9/2012 | Kesler et al. |
| 2013/0069651 A1 | 3/2013 | Lumiani |
| 2013/0099585 A1 | 4/2013 | Von Novak et al. |
| 2013/0116575 A1 | 5/2013 | Mickle et al. |
| 2013/0303970 A1 | 11/2013 | Keenan et al. |
| 2014/0012282 A1 | 1/2014 | Fritsch |
| 2014/0039587 A1 | 2/2014 | Romero |
| 2014/0063666 A1 | 3/2014 | Kallal et al. |
| 2014/0094645 A1 | 4/2014 | Lafontaine et al. |
| 2014/0104898 A1 | 4/2014 | Yeo et al. |
| 2014/0107754 A1 | 4/2014 | Fuhs et al. |
| 2014/0135884 A1 | 5/2014 | Tockman et al. |
| 2014/0194058 A1 | 7/2014 | Lee et al. |
| 2014/0233184 A1 | 8/2014 | Thompson et al. |
| 2014/0249603 A1 | 9/2014 | Yan et al. |
| 2014/0265620 A1 | 9/2014 | Hoarau et al. |
| 2015/0008755 A1 | 1/2015 | Sone |
| 2015/0028805 A1 | 1/2015 | Dearden et al. |
| 2015/0090372 A1 | 4/2015 | Branagan et al. |
| 2015/0196076 A1 | 7/2015 | Billingslea |
| 2015/0290372 A1 | 10/2015 | Muller et al. |
| 2015/0290373 A1* | 10/2015 | Rudser ............... A61M 60/538 623/3.27 |
| 2015/0333532 A1 | 11/2015 | Han et al. |
| 2015/0380972 A1 | 12/2015 | Fort |
| 2016/0022889 A1 | 1/2016 | Bluvshtein et al. |
| 2016/0067395 A1 | 3/2016 | Jimenez et al. |
| 2016/0081680 A1 | 3/2016 | Taylor |
| 2016/0087558 A1 | 3/2016 | Yamamoto |
| 2016/0095968 A1 | 4/2016 | Rudser |
| 2016/0175501 A1 | 6/2016 | Schuermann |
| 2016/0268846 A1 | 9/2016 | Akuzawa et al. |
| 2016/0271309 A1 | 9/2016 | Throckmorton et al. |
| 2016/0331980 A1 | 11/2016 | Strommer et al. |
| 2016/0344302 A1 | 11/2016 | Inoue |
| 2017/0047781 A1 | 2/2017 | Stanislawski et al. |
| 2017/0070082 A1 | 3/2017 | Zheng et al. |
| 2017/0136164 A1 | 5/2017 | Yeatts |
| 2017/0143977 A1 | 5/2017 | Kaib et al. |
| 2017/0202575 A1 | 7/2017 | Stanfield et al. |
| 2017/0203104 A1 | 7/2017 | Nageri et al. |
| 2017/0231717 A1 | 8/2017 | Forsell |
| 2017/0271919 A1 | 9/2017 | Von Novak, Iii et al. |
| 2017/0275799 A1 | 9/2017 | Chen |
| 2017/0288448 A1 | 10/2017 | Kranz et al. |
| 2017/0303375 A1 | 10/2017 | Woodhead |
| 2017/0353053 A1 | 12/2017 | Muratov |
| 2017/0354812 A1 | 12/2017 | Callaghan et al. |
| 2018/0078329 A1 | 3/2018 | Hansen et al. |
| 2018/0194236 A1 | 7/2018 | Elshaer et al. |
| 2018/0207336 A1 | 7/2018 | Solem |
| 2018/0256796 A1 | 9/2018 | Hansen |
| 2018/0256800 A1 | 9/2018 | Conyers et al. |
| 2018/0280708 A1 | 10/2018 | Escalona et al. |
| 2018/0316209 A1 | 11/2018 | Gliner |
| 2019/0004037 A1 | 1/2019 | Zhang et al. |
| 2019/0060543 A1 | 2/2019 | Khanal et al. |
| 2019/0068004 A1 | 2/2019 | Louis |
| 2019/0097447 A1 | 3/2019 | Partovi |
| 2019/0175808 A1 | 6/2019 | Zilbershlag et al. |
| 2019/0222064 A1 | 7/2019 | Du et al. |
| 2019/0344000 A1 | 11/2019 | Kushwaha et al. |
| 2019/0351120 A1 | 11/2019 | Kushwaha et al. |
| 2019/0393735 A1 | 12/2019 | Lee et al. |
| 2020/0054806 A1 | 2/2020 | Sun |
| 2020/0139032 A1 | 5/2020 | Bryson et al. |
| 2020/0227954 A1 | 7/2020 | Ding et al. |
| 2020/0350812 A1 | 11/2020 | Vogt et al. |
| 2021/0052793 A1 | 2/2021 | Struthers et al. |
| 2021/0057804 A1 | 2/2021 | Wenning |
| 2021/0143688 A1 | 5/2021 | Agrawal et al. |
| 2021/0290931 A1 | 9/2021 | Baumbach |
| 2021/0322011 A1 | 10/2021 | Schuelke et al. |
| 2021/0336484 A1 | 10/2021 | Araujo et al. |
| 2021/0379360 A1 | 12/2021 | Schellenberg |
| 2021/0386990 A1 | 12/2021 | Stotz et al. |
| 2021/0393944 A1 | 12/2021 | Wenning |
| 2021/0399582 A1 | 12/2021 | Araujo et al. |
| 2022/0080184 A1 | 3/2022 | Clifton et al. |
| 2022/0080185 A1 | 3/2022 | Clifton et al. |
| 2022/0320901 A1 | 10/2022 | Araujo et al. |
| 2023/0191141 A1 | 6/2023 | Wenning et al. |
| 2023/0352236 A1 | 11/2023 | Diekhans et al. |

FOREIGN PATENT DOCUMENTS

| | | |
|---|---|---|
| CN | 103942511 | 7/2014 |
| CN | 104274873 | 1/2015 |

(56) References Cited

FOREIGN PATENT DOCUMENTS

| | | |
|---|---|---|
| CN | 104888293 | 3/2017 |
| CN | 106776441 | 5/2017 |
| DE | 103 02 550 | 8/2004 |
| DE | 10 2012 200 912 | 7/2013 |
| DE | 11 2012 005 944 | 12/2014 |
| DE | 10 2016 106 683 | 10/2016 |
| DE | 10 2018 206 758 | 11/2019 |
| EP | 0 930 086 | 7/1999 |
| EP | 2 752 209 | 7/2014 |
| EP | 2 782 210 | 9/2014 |
| EP | 2 859 911 | 4/2015 |
| EP | 2 966 753 | 1/2016 |
| EP | 2 454 799 | 9/2016 |
| EP | 2 709 689 | 4/2017 |
| EP | 3 220 505 | 9/2017 |
| EP | 3 357 523 | 1/2021 |
| EP | 3 423 126 | 2/2021 |
| EP | 3 490 628 | 2/2021 |
| EP | 3 198 677 | 3/2021 |
| EP | 3 248 647 | 3/2021 |
| EP | 3 436 106 | 3/2021 |
| EP | 3 509 661 | 3/2021 |
| EP | 3 528 863 | 3/2021 |
| EP | 3 436 105 | 4/2021 |
| EP | 3 116 407 | 5/2021 |
| EP | 3 131 600 | 6/2021 |
| EP | 2 608 731 | 7/2021 |
| EP | 2 599 510 | 10/2021 |
| EP | 3 077 018 | 10/2021 |
| EP | 3 485 936 | 10/2021 |
| EP | 3 539 613 | 2/2022 |
| EP | 2 858 718 | 3/2022 |
| EP | 3 624 867 | 3/2022 |
| EP | 3 755 237 | 4/2022 |
| EP | 3 497 775 | 7/2022 |
| EP | 3 711 788 | 8/2022 |
| EP | 2 654 883 | 9/2022 |
| EP | 3 485 819 | 9/2022 |
| EP | 3 600 477 | 10/2022 |
| EP | 3 808 408 | 11/2022 |
| EP | 3 858 422 | 11/2022 |
| EP | 2 892 583 | 1/2023 |
| EP | 3 597 231 | 1/2023 |
| EP | 3 856 275 | 1/2023 |
| EP | 3 003 420 | 2/2023 |
| EP | 3 946 511 | 4/2023 |
| EP | 3 826 104 | 5/2023 |
| JP | H11-178249 | 7/1999 |
| JP | 2013-013216 | 1/2013 |
| JP | 2018-046708 | 3/2018 |
| KR | 10-1185112 | 9/2012 |
| WO | WO 2008/106103 | 9/2008 |
| WO | WO 2009/023905 | 2/2009 |
| WO | WO 2009/029977 | 3/2009 |
| WO | WO 2010/042054 | 4/2010 |
| WO | WO 2011/007300 | 1/2011 |
| WO | WO 2012/147061 | 11/2012 |
| WO | WO 2013/164831 | 11/2013 |
| WO | WO 2015/152732 | 10/2015 |
| WO | WO 2017/021846 | 2/2017 |
| WO | WO 2017/060257 | 4/2017 |
| WO | WO 2017/066257 | 4/2017 |
| WO | WO 2017/089440 | 6/2017 |
| WO | WO 2017/118738 | 7/2017 |
| WO | WO 2017/165372 | 9/2017 |
| WO | WO 2017/218349 | 12/2017 |
| WO | WO 2018/033799 | 2/2018 |
| WO | WO 2018/100192 | 6/2018 |
| WO | WO 2019/025258 | 2/2019 |
| WO | WO 2019/025259 | 2/2019 |
| WO | WO 2019/025260 | 2/2019 |
| WO | WO 2019/101786 | 5/2019 |
| WO | WO 2019/145253 | 8/2019 |
| WO | WO 2019/158996 | 8/2019 |
| WO | WO 2019/183247 | 9/2019 |
| WO | WO 2019/185511 | 10/2019 |
| WO | WO 2019/185512 | 10/2019 |
| WO | WO 2019/211400 | 11/2019 |
| WO | WO 2019/211405 | 11/2019 |
| WO | WO 2019/211410 | 11/2019 |
| WO | WO 2019/211413 | 11/2019 |
| WO | WO 2019/211414 | 11/2019 |
| WO | WO 2019/211415 | 11/2019 |
| WO | WO 2019/211416 | 11/2019 |
| WO | WO 2019/229224 | 12/2019 |
| WO | WO 2019/234151 | 12/2019 |
| WO | WO 2019/241556 | 12/2019 |
| WO | WO 2019/244031 | 12/2019 |
| WO | WO 2020/089429 | 5/2020 |
| WO | WO 2023/076869 | 5/2023 |

OTHER PUBLICATIONS

International Preliminary Report on Patentability and Written Opinion received in PCT/EP2019/061321, dated Aug. 17, 2020 in 29 pages.
Atkinson et al., "Pulse-Doppler Ultrasound and Its Clinical Application", The Yale Journal of Biology and Medicine, 1977, vol. 50, pp. 367-373.
Leguy et al., "Assessment of Blood vol. Flow in Slightly Curved Arteries from a Single Velocity Profile", Journal of Biomechanics, 2009, pp. 1664-1672.
Murali, Akila, "Design of Inductive Coils for Wireless Power Transfer to Pediatric Implants", A graduate project submitted in partial fulfillment of the requirements For the degree of Master of Science in Electrical Engineering, California State University, Northridge, May 2018, pp. 37.
Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.
Vieli, A., "Doppler Flow Determination", BJA: British Journal of Anaesthesia, 1988, vol. 60, pp. 107S-112S.

* cited by examiner

TRANSMISSION UNIT COMPRISING A TRANSMISSION COIL AND A TEMPERATURE SENSOR

The invention relates to a transmitter unit comprising a housing, comprising a transmitter coil disposed in said housing for inductively transferring electrical energy to a receiver unit, which is disposed in a part of the body of a person, in particular a patient, e.g. in the tissue of a body of a patient, and comprises a receiver coil, when a contact surface of said housing is in contact with the body, and comprising a control device for controlling the operation of the transmitter coil.

The invention also relates to a method for determining the local temperature of a body of a person, in particular a patient, on a surface, e.g. the temperature of the tissue of the body on a surface, through which electrical energy for supplying an electrical consumer disposed in the tissue of the body is inductively transferred and to a method for inductively transferring electrical energy. The invention in particular relates to a method for determining the temperature on a surface in an apparatus for inductively transferring energy. The invention further relates to an apparatus which is operated according to a method according to the invention as well as the use of the method according to the invention.

In the medical field, methods for inductively transferring energy, in which an energy store in the form of a rechargeable battery disposed inside a body can be charged by inductive means, are already well-known in the state of the art (DE 10 2016 106 683 A1). For this purpose, a receiver coil disposed in a receiver unit inside the body of a patient cooperates with a transmitter coil disposed in a transmitter unit outside the body. Between the receiver coil and the transmitter coil, which are positioned at a defined, relatively small distance to one another, there is human tissue or the skin of the patient. During the operation of the transmitter coil, the tissue of the patient between the receiver unit and the transmitter unit is warmed, in particular as a result of thermal losses in the transmitter unit and in the receiver unit. The level of warming is limited for health reasons and may not exceed a certain amount.

The object of the invention is to enable the inductive transfer of electrical energy to a powerful electrical consumer or electrical energy store disposed, for example, in the body of a patient, without damaging the tissue of the patient.

This object is achieved by the transmitter unit specified in Claim 1 and the methods specified in Claim 18 and Claim 20.

Advantageous embodiments of the invention are specified in the dependent claims.

The invention is based on the idea that monitoring the temperature of the surface of a patient in the region of direct contact with the transmitter unit makes it possible to infer information about the warming of the tissue of the patient.

One finding of the invention is that the measurement signals of a temperature sensor, which is disposed as close as possible to the to-be-measured surface, are affected by the inductive transfer of electrical energy. It is evident that, during operation of the transmitter coil, not only the (human) tissue or the skin surface of the patient is warmed, but that the magnetic fields produced by the transmitter coil also warm the temperature sensor or its leads, which results in a measurement error. Taking into account a not-to-be-exceeded (limit) temperature of the tissue in the transfer region of the apparatus, this then means that the operation of the transmitter coil is not optimized yet, or the registered temperature does not correspond to the actual temperature on the to-be-measured surface of the patient.

The invention has the advantage that it makes optimum use of the foreseen (allowable) maximum temperature increase of the tissue of the patient in the effective region of the transmitter unit or the transmitter coil, and thus makes it possible to optimize or maximize the transfer of energy into the receiver coil. This then enables short charging times for an electrical energy store, e.g. in the form of a rechargeable battery, disposed in the body of the patient, for example, or the possibility of reducing the time the externally disposed transmitter unit or transmitter coil is worn on the body.

One idea of the invention is that the component of the warming of the temperature sensor caused by the fields of the transmitter coil of the transmitter unit is taken into account when the temperature of the to-be-measured surface is registered. Taking into account the component of the warming of the temperature sensor caused by the (magnetic) fields emitted by the transmitter coil therefore reduces the temperature on the surface determined by the temperature sensor, which results in longer operating times, and/or makes it possible to set stronger magnetic fields of the transmitter coil, before a specific not-to-be-exceeded temperature limit value on the to-be-measured surface is actually reached.

In a variant of the method as described thus far, it can be provided that the component of the warming of the temperature sensor or its input leads is taken into account as a fixed value resulting from taking into account a given maximum operating time of the apparatus and given environmental parameters. This means that it has been determined, in particular on the basis of series of tests, by what amount of temperature the temperature sensor is warmed when it is exposed to a typical maximum operating time of the transmitter coil, taking into account a typical maximum outside temperature, for example. If this value is 0.8 Kelvin, for example, this maximum temperature increase of the temperature sensor (0.8 Kelvin) is subtracted from the respective value of the temperature on the surface currently registered by the temperature sensor, to thereby infer the actual maximum prevailing temperature on the surface.

In a further variant modified from the variant described above, an actually existing warming of the temperature sensor resulting from the operation of the transmitter coil can be taken into account by determining the component of the warming of the temperature sensor taking into account the registered temperature progression of the sensed surface after the operation of the transmitter coil of the apparatus has been stopped. This means that, after the operation of the transmitter coil of the apparatus is stopped, the temperature sensor continues to register the temperature on the to-be-measured surface and delivers it as input values to the control device of the apparatus. The actually existing temperature on the to-be-measured surface at the time the operation of the transmitter coil is stopped can be inferred using the temperature drop that occurs over time and is caused, on the one hand, by the no longer occurring transfer of heat into the human body and, on the other hand, by the heat dissipation from the temperature sensor.

In a further development of this method, it is provided that the operation of the transmitter coil is stopped periodically. The temperature on the to-be-measured surface of the patient can thus be monitored throughout the entire charging phase or the phase in which energy is transferred from the transmitter coil to the receiver coil.

There are a number of different ways to infer the actual temperature of the to-be-measured surface. In a first, particularly preferred method, the component of the warming of the temperature sensor caused by the operation of the transmitter coil is determined on the basis of a mathematical function taking into account known parameters of the temperature sensor and, if applicable, environmental parameters. Known parameters of the temperature sensor are in particular understood to be its heat storage capacity, its placement inside the housing of the transmitter unit, and thus its heat dissipation or cooling. Environmental parameters are in particular understood to be the external ambient temperature in the region of the transmitter unit and, if applicable, the current body temperature of the patient. The mentioned parameters of the temperature sensor and the apparatus or the housing of the apparatus and the ambient temperature can be brought into a mathematical relationship, for example using series of tests, such that, for example, a specific cooling function of the temperature sensor is established at a specific ambient temperature. This function can therefore be used to extrapolate or estimate the actual temperature on the to-be-measured surface at the time the transmitter coil is switched off.

In an alternative configuration of the method, however, it can also be provided that the temporal progression of the temperature registered by the temperature sensor after the transmitter coil is switched off is compared to curve progressions stored in the control device and, if it matches or approximates a stored curve progression, the actual temperature in the region of the to-be-measured surface at the time the transmitter coil is switched off can be inferred.

For a further optimization of the energy transfer to shorten charging times or to achieve the highest possible charging rates for the electrical energy store disposed in the patient, it is proposed that the apparatus for inductively transferring energy is controlled on the basis of the determined temperature, and that the transmitter coil is periodically not operated to avoid the occurrence of excessively high temperatures, wherein the duration of the operating breaks of the transmitter coil is based on the determined temperature on the surface. This means that the length of the operating breaks is selected to be such that they last only until the registered temperature is at a specific minimum separation from the limit value. The temperature on the to-be-measured surface is thus always kept just below the limit temperature, which overall enables an optimization of the energy transfer. Alternatively, it is also possible to throttle or adjust the transmission power to keep the temperature constant without operating breaks.

The invention also includes an apparatus for inductively transferring energy comprising a transmitter coil disposed in a housing, wherein the housing can be positioned at least in indirect contact with the to-be-measured surface, and wherein the apparatus is operated according to a method, in which the component of the warming of the temperature sensor is determined taking into account the registered temperature progression of the sensed surface after the operation of the transmitter coil of the apparatus is stopped. According to the invention, this apparatus comprises a temperature sensor, which can be exposed to the electromagnetic field of the transmitter coil so that said sensor is disposed in an operative connection with said coil. The apparatus can comprise an algorithm for determining the component of the warming of the temperature sensor or its input leads caused by the transmitter coil.

For the sake of making the apparatus as compact as possible, it is preferably provided that the temperature sensor is of an SMD design.

Lastly, the invention also includes the use of a method according to the invention as described thus far for determining the skin and/or tissue temperature in a human body during a transfer of energy into the human body, in particular with a VAD (ventricular assist device) system.

Further advantages, features and details of the invention emerge from the following description of preferred design examples. These are shown schematically in the drawings and are described below.

The figures show.

The same elements or elements having the same function are provided with the same reference signs in the figures.

Figure 1:
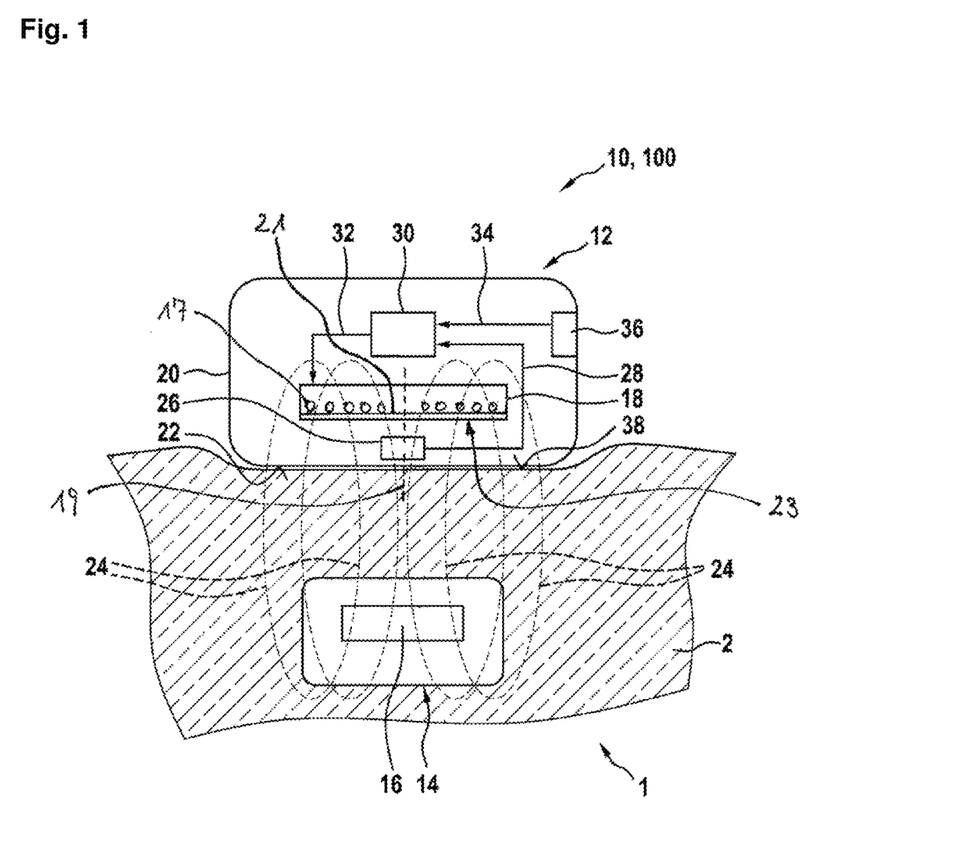
FIG. 1 an apparatus for inductively transferring energy comprising a transmitter coil and comprising a temperature sensor, which is used for inductively transferring energy into a receiver unit having a receiver coil in a VAD system disposed in a human body.

FIG. 1 shows the essential components of an apparatus 10 for inductively transferring energy on a receiver unit 14 disposed in the body 1 of a patient and having a receiver coil 16 in a highly simplified manner. The apparatus 10 is in particular a component of a cardiac support system in the form of a so-called ventricular assist device system (VAD system) 100. The VAD system 100 in particular includes a pump disposed in the body 1 of the patient, which supports the patient's heart function. In the body 1 of the patient, this pump is operated with electrical energy from an electrical energy store not shown in FIG. 1, e.g. a rechargeable battery, which is connected to the receiver unit 14. This electrical energy store has to be charged due to the energy consumption of the pump. By inductively transferring energy into the receiver unit 14 by means of the apparatus 10, the electrical energy store connected to the receiver unit 14 is charged.

The apparatus 10 comprises a transmitter unit 12 outside the body 1 of the patient and the receiver unit 14 with the receiver coil 16 disposed inside the body 1 of the patient. It should be noted that the receiver unit 14 may in principle comprise a plurality of receiver coils 16.

Between the transmitter unit 12 and the receiver unit 14 there is human tissue 2 or the skin of the patient. The receiver coil 16 is disposed in operative connection with the electrical energy store to be charged. The receiver coil 16 cooperates with a transmitter coil 18 disposed in the transmitter unit 12. The transmitter coil 18 is disposed inside a housing 20 of the transmitter unit 12, whereby the housing 20 is disposed at least in indirect contact with the body 1 or the tissue 2 in the region of a contact surface 22 of the housing 20.

The transmitter coil 18 has a coil winding 17, which comprises conductor loops disposed around a coil axis 19 that passes through the contact surface 22. The coil winding 17 of the transmitter coil 18 is located on a transmitter coil carrier 21, which extends in a planar manner and through which the coil axis 19 passes, and which has a carrier surface that faces the contact surface 22 of the housing 20 for the coil turns of the transmitter coil 18.

To operate the apparatus 10, it is also necessary for the receiver coil 16 and the transmitter coil 18 to be aligned with one another in order to be able to produce a magnetic field when current is supplied to the transmitter coil 18. The field lines 24 of this magnetic field, which are shown in FIG. 1, lead to the induction of an electrical voltage and thus to the flow of an electrical current in the receiver coil 16, which can then be used to charge the electrical energy store.

During operation of the transmitter coil 18, the tissue 2 of the body 1 located between the transmitter unit 12 and the receiver unit 14 is warmed by the loss-related warming of the transmitter unit 12 and the receiver unit 14. This warming of tissue 2 has to be limited to avoid physical impairments or damage and/or to comply with legal standards.

For this purpose, it is provided that the temperature of the tissue 2 in the region of contact of the housing 20 of the transmitter unit 12 with the tissue 2 is monitored by means of a temperature sensor 26 in the region of a measurement surface 38 on the surface of the tissue 2.

The temperature sensor 26 is disposed in the housing 20 of the transmitter unit 12 on a side 23 of the transmitter coil 18 facing the contact surface 22.

To make the design as compact as possible, it is in particular provided that the temperature sensor 26 is designed as an SMD component or an SMD assembly. The temperature sensor 26 is connected to a control device 30 of the transmitter unit 12 via an electrical lead 28. The control device 30 is also used to control the transmitter coil 18 via a lead 32. A further lead 34 connects the control device 30 to a further temperature sensor 36, which is configured to register the ambient temperature outside the transmitter unit 12.

As can be seen in FIG. 1, both the temperature sensor 26 and, if applicable, the lead 28 are disposed in operative connection with the magnetic field lines 24 of the transmitter coil 18. As a result, during operation of the transmitter coil 18, not only the tissue 2 is warmed, in particular by the lost heat from the transmitter unit 12 and the receiver unit 14, but also the temperature sensor 26 or the lead 28, in particular by the magnetic field of the transmitter coil 18, which can lead to the temperature sensor 26 heating up more than the surrounding tissue 2. This in turn has the consequence that the temperature increase of said components leads to a measurement error, which manifests itself in that the temperature T registered by the temperature sensor 26 in the region of the measurement surface 38 is falsified or increased by the measurement error.

To detect or take into account this measurement error or to register the actual temperature T on the measurement surface 38 of the body 1, the transmitter coil 18 is operated in a specific manner. For clarification, reference is made to FIG. 2.

Figure 2:
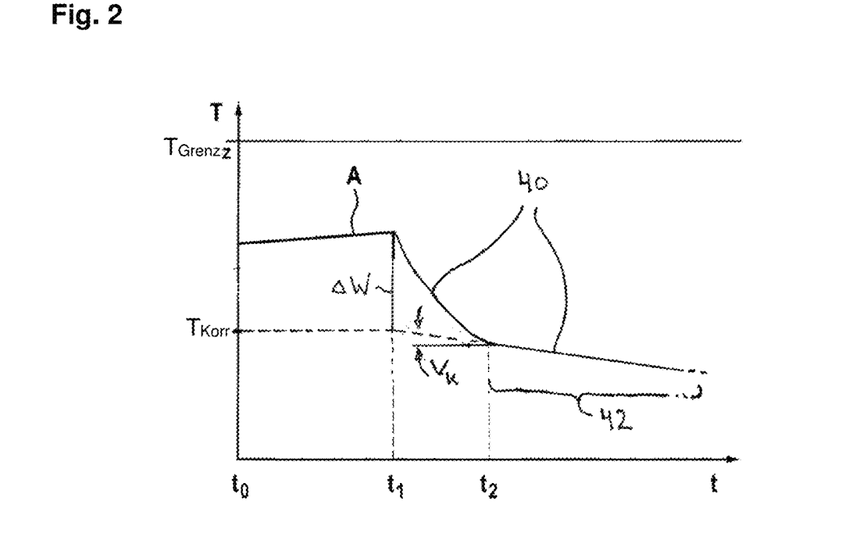
FIG. 2 a first diagram with the temporal progression of a temperature T registered by the temperature sensor in the apparatus for inductively transferring energy and with a limit temperature $T_{Grenz}$, and FIG. 3 a second diagram with the temporal progression of a temperature T registered by the temperature sensor in the apparatus for inductively transferring energy and with a limit temperature $T_{Grenz}$.

FIG. 2 shows the temperature T registered by the temperature sensor 26 in the apparatus 10 at the time t as a curve progression A. The temperature sensor 26 transmits the temperature T registered at the time t to the control device 30.

The temperature T increases slightly in the period between $t_0$ and $t_1$. The increase in temperature T can be explained by the fact that, during operation of the transmitter coil 18, both the temperature in the tissue 2 and the temperature in the temperature sensor 26 or the lead 28 is increased by the effect of the temporally changing magnetic field produced by the transmitter coil 18, which causes eddy currents. However, the temperature T is below a limit temperature $T_{Grenz}$ that has to be observed. At the time point $t_1$, the operation of the transmitter coil 18 is now stopped by the control device 30. The curve progression A then shows that the temperature T, which continues to be registered by the temperature sensor 26 and delivered to the control device 30 as an input quantity, decreases with the decay curve 40.

The curve progression A after the time point $t_1$ results from both the now absent warming of the tissue 2, or its cooling, and from the heat dissipation or cooling of the temperature sensor 26 and the lead 28.

An algorithm with a mathematical function is stored in the control device 30 of the transmitter unit 12 or the apparatus 10, which makes it possible to infer the actual temperature T in the region of the measurement surface 38 at the time point $t_1$ based on the values of the temperature T after the time point $t_1$, for example by extrapolation from the cooling rate $V_K$ at a time point $t_2$ after the time point $t_1$. This makes use of the fact that, due to its size, the temperature sensor 26 has a significantly lower heat storage capacity than the surrounding tissue 2 and the surface of the housing 20. As a result, there is a dynamic drop in the temperature T immediately after the transmitter coil 18 is switched off at the time point $t_1$. Once this temporary equalization process is completed at the time point $t_2$, the temperature sensor 26 registers the actual temperature T of the tissue 2, because the low heat storage capacity of the temperature sensor 26 has been "discharged". The mentioned extrapolation of the cooling curve at the switch-off time $t_1$ can therefore be used to infer the actual temperature at the switch-off time $t_1$. The additional warming of the temperature sensor 26 is thus taken into account or eliminated.

Alternatively, it can be provided that the curve progression A after the time point $t_1$ is compared to curve progressions stored in the control device 30, and, if it matches or approximates a stored curve progression, the respective temperature $T_{Korr}$ at the measurement surface 38 of the body 1 at the time point $t_1$ is inferred. The difference between the corrected temperature $T_{Korr}$ on the measurement surface 38 and the temperature T registered at the time point $t_1$ is the component $\Delta W$ caused by the warming of the temperature sensor 26 and the lead 28.

As soon as the temperature T on the measurement surface 38, which has been corrected by the amount of warming of the temperature sensor 26 or the lead 28 caused by the operation of the transmitter coil 18, has been determined, the control device 30 again actuates the transmitter coil 18 in order to enable a further transfer of energy. In order to enable continuous monitoring of the (actual) temperature T on the measurement surface 38, the switching off or switching on of the transmitter coil 18 as described thus far is preferably carried out periodically, i.e. at regular intervals.

Figure 3:
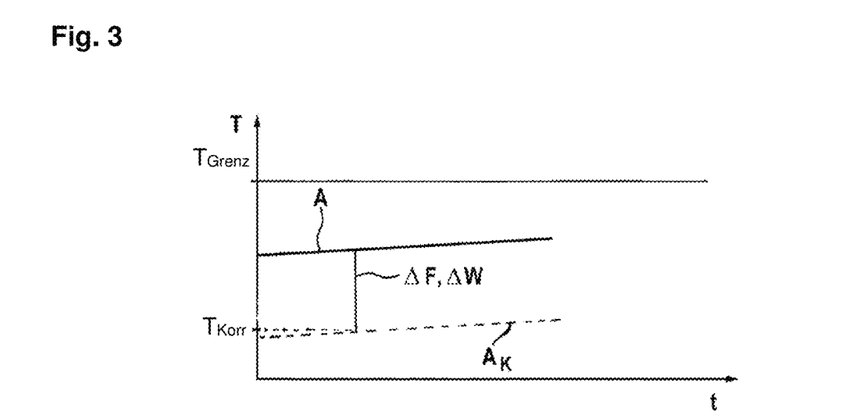

FIG. 3 shows a diagram that illustrates a simplified measurement procedure. Here, the temperature T registered by the temperature sensor 26 is again shown over the time t. A continuous, i.e. uninterrupted, operation of the transmitter coil 18 is assumed. The values of the temperature T transmitted by the temperature sensor 26 to the control device 30 are indicated by the curve progression A. The curve progression $A_K$ shows a corrected curve progression A taking into account a fixed value OF as the component $\Delta W$, which is assumed to be the maximum possible measurement error resulting from the warming of the temperature sensor 26 and the lead 28 due to the warming caused by the operation of the transmitter coil 18. In other words, this means that the control device 30 assumes that the temperature T calculated using the $A_K$ is the highest possible temperature that can be present on the measurement surface 38.

Of course, in both methods it is respectively assumed that the operation of the apparatus 10 or the transmitter coil 18 is stopped when a limit temperature $T_{Grenz}$ is approached, for example until the determined temperature T has a specific separation from the limit temperature $T_{Grenz}$.

The methods as described thus far can be altered or modified in a variety of ways without departing from the idea of the invention. It should in particular be noted that the described methods are not limited to use in a VAD system 100.

In summary, the following preferred features of the invention should in particular be noted:

A transmitter unit 12 comprises a housing 20 and a transmitter coil 18 disposed in said housing 20 for inductively transferring electrical energy to a receiver unit 14, which is disposed in the tissue 2 of the body 1 of a patient and comprises a receiver coil 16, when a contact surface 22 of said housing 20 is in contact with the body 1. The transmitter unit 12 comprises a control device 30 for controlling the operation of the transmitter coil 18. The transmitter unit comprises a temperature sensor 26 for determining a local warming of the body 1 caused by the inductive transfer of electrical energy into the receiver unit 14. The invention also relates to methods for determining the temperature ($T_{Korr}$) of a body 1 on a surface 38 through which electrical energy for supplying an electrical energy store or an electrical consumer disposed in the body 1 is inductively transferred and to a method for inductively transferring electrical energy.

The invention relates, in particular, to the aspects specified in the following clauses:

1. Method for determining the temperature (T) on a surface (38) in apparatus (10) for inductively transferring energy, wherein the apparatus (10) comprises a transmitter coil (18) disposed in a housing (20) and the housing (20) is disposed at least in indirect contact with the to-be-measured surface (38), and comprising a temperature sensor (26) for registering the temperature (T) of the surface (38), wherein the temperature sensor (26) and, if applicable, the electrical lead (28) of said sensor is disposed in operative connection with the transmitter coil (18), such that, during operation of the transmitter coil (18), the temperature sensor (26) and, if applicable, the electrical lead (28) of said sensor is warmed by the fields emitted by the transmitter coil (18), so that the temperature (T) registered by the temperature sensor (26) includes a component ($\Delta W$) that results from the warming of the temperature sensor (26) and, if applicable, the electrical lead (28) of said sensor by the transmitter coil (18), and wherein the component ($\Delta W$) resulting from the transmitter coil (18) is taken into account in the registering of the temperature (T) of the measurement surface (38).
2. Method according to clause 1, characterized in that that the component ($\Delta W$) is taken into account as a fixed value ($\Delta F$), which is obtained by taking into account a given maximum operating time of the apparatus (10) and given environmental parameters.
3. Method according to clause 1, characterized in that the component ($\Delta W$) of the warming is determined taking into account the registered temperature progression (A) of the sensed surface (38) after the operation of the transmitter coil (18) of the apparatus (10) is stopped.
4. Method according to clause 3, characterized in that the operation of the transmitter coil (18) is stopped periodically.
5. Method according to clause 3 or 4, characterized in that the component of the warming ($\Delta W$) is determined on the basis of a mathematical function, taking into account known parameters of the temperature sensor (26), such as its heat storage capacity storage capacity, and, if applicable, environmental parameters.
6. Method according to clause 3 or 4, characterized in that the component of the warming ($\Delta W$) is based on a comparison of the temperature progression (A) on the sensed surface (38) with stored curve progressions.
7. Method according to any one of clauses 1 to 6, characterized in that the apparatus (10) for inductively transferring energy is controlled on the basis of the determined temperature (T) and the transmitter coil (18) is periodically not operated to avoid the occurrence of excessively high temperatures (T), wherein the duration of the operating breaks of the transmitter coil (18) is based on the determined temperature (T) on the surface (38).
8. Apparatus (10) for inductively transferring energy, comprising a transmitter coil (18) disposed in a housing (20), wherein the housing (20) can be positioned at least in indirect contact with a to-be-measured surface (38), wherein the apparatus (10) is operated according to a method according to any one of Clauses 3 to 7, characterized in that a temperature sensor (26) is disposed in operative connection with the transmitter coil (18), and that the apparatus (10) comprises an algorithm for determining the component ($\Delta W$) of a warming of the temperature sensor (26) and, if applicable, the lead (28) of said sensor caused by the fields emitted by the transmitter coil (18).
9. Apparatus according to clause 8, characterized in that the temperature sensor (26) is of an SMD design.
10. Use of the method according to any one of clauses 1 to 7 for determining the skin and/or tissue temperature of a human body (1) during an energy transfer in the human body (1), in particular in a VAD system (100).

LIST OF REFERENCE SKINS

1 Body
2 Human tissue
10 Apparatus
12 Transmitter unit
14 Receiver unit
16 Receiver coil
17 Coil winding
18 Transmitter coil
19 Coil axis
20 Housing
21 Transmitter coil carrier
22 Contact surface
23 Side
24 Field line
26 Temperature sensor
28 Electrical lead
30 Control device
32 Lead
34 Further lead
36 Further temperature sensor
38 Measurement surface
40 Decay curve
42 Section
100 Ventricular assist device (VAD) system
A Curve progression
$A_K$ Corrected curve progression
T Temperature
$T_{Grenz}$ Limit temperature
$T_{Korr}$ Corrected temperature
t Time $V_K$ Cooling rate
$\Delta W$ Component
$\Delta F$ Fixed value

The invention claimed is:

1. A transmitter unit comprising:
a transmitter coil configured to inductively transfer electrical energy to a receiver unit disposed in a living body;
a temperature sensor configured to determine an increase in local temperature of the living body caused by the inductive transfer of electrical energy to the receiver unit; and
a control device configured to control operation of the transmitter coil based at least in part on the increase in local temperature of the living body,
wherein the control device stores a temperature determination routine configured to determine a local temperature at a surface of the living body based at least in part on temperature measurement signals of the temperature sensor and accounting for warming of the temperature sensor caused by the transmitter coil.

2. The transmitter unit of claim 1 further comprising a housing, wherein the transmitter coil is disposed in the housing and the temperature sensor is positioned between the transmitter coil and a contact surface.

3. The transmitter unit of claim 1, wherein the temperature determination routine is configured to account for an operating state of the transmitter coil.

4. The transmitter unit of claim 1, wherein the temperature determination routine is configured to stop the operation of the transmitter coil at a first time point.

5. The transmitter unit of claim 1, wherein the warming of the temperature sensor is caused by eddy currents.

6. The transmitter unit of claim 5, wherein the temperature determination routine contains an algorithm, wherein the algorithm is configured to calculate the local temperature at the surface of the living body based at least in part on extrapolation of a decay curve from a second time point following a first time point to the first time point.

7. The transmitter unit of claim 6, wherein the algorithm is configured to calculate the local temperature at the surface of the living body based at least in part on extrapolation of a decay curve from a second time point following the first time point to the first time point.

8. The transmitter unit of claim 6, wherein the algorithm is configured to linearly extrapolate a progression of the decay curve from a second time point to the first time point.

9. The transmitter unit of claim 6, wherein the algorithm is configured to subtract a fixed correction value from temperature values corresponding to the temperature measurement signals.

10. The transmitter unit of claim 1, wherein the control device stores a shutdown routine configured to stop the operation of the transmitter coil, wherein the shutdown routine is configured to prevent or reduce the inductive transfer of electrical energy to the receiver unit when the local temperature determined by the temperature determination routine exceeds a threshold value.

11. A system comprising:
a temperature sensor;
a transmitter coil;
a memory storing computer-readable instructions; and
a processor configured to communicate with the temperature sensor, the transmitter coil, and the memory, wherein the computer-readable instructions, when executed, cause the processor to:
prevent an inductive transfer of electrical energy from the transmitter coil at a first time point;
determine a first temperature of a surface of a living body a second time point following the first time point;
and
calculate a local temperature of the surface of the living body based at least in part on temperature measurement signals of the temperature sensor and accounting for warming of the temperature sensor caused by the transmitter coil.

12. The system of claim 11 the computer-readable instructions further comprising:
determine a decay curve based at least in part on the first temperature measured at a second time point following the first time point.

13. The system of claim 12, wherein the calculation uses an algorithm, wherein the algorithm is configured to determine the local temperature of the surface of the living body at least in part by extrapolating a progression of a section of the decay curve from the second time point following the first time point to the first time point.

14. The system of claim 13, wherein the algorithm is configured to extrapolate the progression of the section of the decay curve based at least in part on a comparison of the decay curve with one or more decay curve progressions stored in the memory.

15. The system of claim 13, wherein the algorithm is configured to linearly extrapolate the progression of the decay curve from the second time point to the first time point.

16. The system of claim 12, wherein the preventing the inductive transfer of electrical energy from the transmitter coil at the first time point, the measuring the temperatures at the surface at a second time point following the first time point, the determining the decay curve from the temperatures measured at the first time point, and the calculating the local temperature at the surface of the living body based at least in part on the decay curve and an algorithm configured to account for an effect of inductive transfer of electrical energy from the transmitter coil to an electrically powered device are repeated continuously.

17. A method for determining a local temperature at a surface of a living body, wherein electrical energy for an electrical energy storage or an electrically powered device disposed in the living body is inductively transferred through the surface, the method comprising:
preventing an inductive transfer of the electrical energy at a first time point;
determining temperatures measured at the surface at a plurality of time points following the first time point;
and
calculating the local temperature at the surface based at least in part on temperature measurement signals of a temperature sensor and accounting for warming of the temperature sensor caused by a transmitter coil.

18. The method of claim 17 further comprising:
determine a decay curve based at least in part on the temperatures measured at a second time point of the plurality of time points following the first time point.

19. The method of claim 17, wherein the calculation uses an algorithm, wherein the algorithm is configured to determine the local temperature of the surface of the living body at least in part by extrapolating a progression of a section of a decay curve from a second time point of the plurality of time points following the first time point to the first time point.

20. The method of claim 19, wherein the algorithm is configured to extrapolate the progression of the section of the decay curve based at least in part on a comparison of the decay curve to one or more decay curve progressions stored in a data memory.

* * * * *

UNITED STATES PATENT AND TRADEMARK OFFICE
CERTIFICATE OF CORRECTION

| | | |
|---|---|---|
| PATENT NO. | : 12,102,835 B2 | Page 1 of 1 |
| APPLICATION NO. | : 18/231517 | |
| DATED | : October 1, 2024 | |
| INVENTOR(S) | : Ingo Stotz | |

It is certified that error appears in the above-identified patent and that said Letters Patent is hereby corrected as shown below:

On the Title Page

In Column 1, Line 24, under U.S. Patent Documents, delete "Benkowski et al." and insert --Benkowsi et al.--.

In the Specification

In Column 4, Line 19, delete "temperature $T_{Grenz}$, and" and insert --temperature $T_{Grenz}$; and--.

In Column 6, Line 56, delete "value OF as" and insert --Value $\Delta F$ as--.

In Column 8, Line 36 (Approx.), delete "SKINS" and insert --SIGNS--.

Signed and Sealed this
Twenty-eighth Day of January, 2025

Coke Morgan Stewart
*Acting Director of the United States Patent and Trademark Office*